United States Patent
Voorhees

(10) Patent No.: US 8,697,434 B2
(45) Date of Patent: Apr. 15, 2014

(54) DETECTION OF PHAGE AMPLIFICATION BY SERS NANOPARTICLES

(75) Inventor: Kent J. Voorhees, Golden, CO (US)

(73) Assignee: Colorado School of Mines, Golden, CO (US)

( * ) Notice: Subject to any disclaimer, the term of this patent is extended or adjusted under 35 U.S.C. 154(b) by 750 days.

(21) Appl. No.: 12/351,522

(22) Filed: Jan. 9, 2009

(65) Prior Publication Data

US 2009/0246753 A1  Oct. 1, 2009

Related U.S. Application Data

(60) Provisional application No. 61/020,454, filed on Jan. 11, 2008.

(51) Int. Cl.
*C12M 1/36* (2006.01)

(52) U.S. Cl.
USPC ................................. 435/287.9; 435/287.1

(58) Field of Classification Search
USPC .......................................... 435/287.1, 287.9
See application file for complete search history.

(56) References Cited

U.S. PATENT DOCUMENTS

| | | |
|---|---|---|
| 3,839,175 A | 10/1974 | Keyes |
| 4,104,126 A | 8/1978 | Young |
| 4,764,473 A | 8/1988 | Matschke |
| 4,797,363 A | 1/1989 | Teodorescu et al. |
| 4,861,709 A | 8/1989 | Ulitzur et al. |
| 5,085,982 A | 2/1992 | Keith |
| 5,101,105 A | 3/1992 | Fenselau et al. |
| 5,126,024 A | 6/1992 | Bonelli et al. |
| 5,135,870 A | 8/1992 | Williams et al. |
| 5,168,037 A | 12/1992 | Entis et al. |
| 5,443,987 A | 8/1995 | Decicco et al. |
| 5,445,942 A | 8/1995 | Rabin et al. |
| 5,469,369 A | 11/1995 | Rose-Pehrsson et al. |
| 5,476,768 A | 12/1995 | Pearson et al. |
| 5,498,525 A | 3/1996 | Rees et al. |
| 5,498,528 A | 3/1996 | King |
| 5,550,062 A | 8/1996 | Wohltjen et al. |
| 5,620,845 A | 4/1997 | Gould et al. |
| 5,656,424 A | 8/1997 | Jurgensen et al. |
| 5,658,747 A | 8/1997 | Feldsine et al. |
| 5,679,510 A | 10/1997 | Ray et al. |
| 5,710,005 A | 1/1998 | Rittenburg |
| 5,723,330 A | 3/1998 | Rees et al. |
| 5,766,840 A | 6/1998 | Kim et al. |
| 5,789,174 A | 8/1998 | Mouton et al. |
| 5,824,468 A | 10/1998 | Scherer et al. |
| 5,859,375 A | 1/1999 | Danylewych-May et al. |
| 5,874,226 A | 2/1999 | Zeytinoglu et al. |
| 5,888,725 A | 3/1999 | Sanders |
| 5,914,240 A | 6/1999 | Sanders |
| 5,958,675 A | 9/1999 | Wicks et al. |
| 5,985,596 A | 11/1999 | Wilson |
| 6,004,770 A | 12/1999 | Nelson |
| 6,037,118 A | 3/2000 | Thomas et al. |
| 6,090,541 A | 7/2000 | Wicks et al. |
| 6,093,541 A | 7/2000 | Nelson |
| 6,177,266 B1 | 1/2001 | Krishnamurthy et al. |
| 6,183,950 B1 | 2/2001 | Voorhees et al. |
| 6,235,480 B1 | 5/2001 | Shultz et al. |
| 6,265,169 B1 | 7/2001 | Cortese et al. |
| 6,300,061 B1 | 10/2001 | Jacobs, Jr. et al. |
| 6,316,266 B1 | 11/2001 | Nelson |
| 6,322,783 B1 | 11/2001 | Takahashi |
| 6,355,445 B2 | 3/2002 | Cherwonogrodzky et al. |
| 6,428,976 B1 | 8/2002 | Chang et al. |
| 6,436,652 B1 | 8/2002 | Cherwonogrodzky et al. |
| 6,436,661 B1 | 8/2002 | Adams et al. |
| 6,461,833 B1 | 10/2002 | Wilson |
| 6,514,767 B1 | 2/2003 | Natan |
| 6,514,778 B2 | 2/2003 | Huang |
| 6,524,809 B1 | 2/2003 | Wilson |
| 6,544,729 B2 | 4/2003 | Sayler et al. |
| 6,555,312 B1 | 4/2003 | Nakayama |
| 6,580,068 B1 | 6/2003 | Tarver et al. |
| 6,660,437 B2 | 12/2003 | Friedrich et al. |
| 6,660,470 B1 | 12/2003 | Sanders |
| 6,787,360 B2 | 9/2004 | Agrawal et al. |
| 6,799,119 B1 | 9/2004 | Voorhees et al. |
| 6,824,975 B2 | 11/2004 | Hubscher et al. |
| 6,913,753 B2 | 7/2005 | Ramachandran |
| 7,034,113 B2 | 4/2006 | Olstein |
| 7,087,376 B2 | 8/2006 | Miller |
| 7,166,425 B2 | 1/2007 | Madonna et al. |
| 7,195,778 B2 | 3/2007 | Flashner-Barak et al. |
| 2002/0192676 A1 | 12/2002 | Madonna et al. |

(Continued)

FOREIGN PATENT DOCUMENTS

| | | |
|---|---|---|
| DE | 43 14998 | 11/1994 |
| EP | 0 168 933 | 2/1986 |

(Continued)

OTHER PUBLICATIONS

Mulvaney et al. "Glass-coated, analyte-tagged nanoparticles: a new tagging system based on detection with surface-enhanced Raman scattering", Langmuir, 2003, 19:4784-4790.*
Lin et al. "Development of a nanoparticle-labeled microfluidic immunoassay for detection of pathogenic microorganisms", Clinical and Diagnostic Laboratory Immunology, 2005, 12(3):418-425.*
Zhu et al. "Binary nanomaterials based on nanocarbons: a case for probing carbon nanohorns' biorecognition properties", Nano Letters, 2003, 3(8):1033-1036.*
Passivating oxide definition: 1 page, 2011.*
Abbas-Hawks et al., "In Situ Methylation of Nucleic Acids Using Pyrolysis/Mass Spectrometry," Rapid Communications in Mass Spectrometry, vol. 10, pp. 1802-1806, 1996.
Abdel-Hamid et al., "Flow-through immunofiltration assay system for rapid detection of *E. coli* O157:h7," *Biosens. Bioelectron.*, 1999, vol. 14, No. 3, pp. 309-316.
Barringer Research Limited, "Biological Agent Detection by Ion Mobility Spectrometery (Final Report)," CR96-012, pp. 1-25, Apr. 1996.

(Continued)

*Primary Examiner* — Bin Shen
(74) *Attorney, Agent, or Firm* — Dorsey & Whitney LLP

(57) ABSTRACT

A phage specific antibody presenting particle, devices and methods related to detection of phage amplification are provided.

14 Claims, 3 Drawing Sheets

(56) References Cited

U.S. PATENT DOCUMENTS

| | | |
|---|---|---|
| 2003/0175207 A1 | 9/2003 | Olstein et al. |
| 2004/0002126 A1 | 1/2004 | Houde et al. |
| 2004/0121403 A1 | 6/2004 | Miller |
| 2004/0137430 A1 | 7/2004 | Anderson et al. |
| 2005/0003346 A1 | 1/2005 | Voorhees et al. |
| 2005/0208475 A1 | 9/2005 | Best et al. |
| 2005/0250096 A1 | 11/2005 | Wheeler et al. |
| 2005/0255043 A1 | 11/2005 | Hnatowich et al. |
| 2007/0059725 A1 | 3/2007 | Voorhees |
| 2007/0148638 A1 | 6/2007 | Madonna et al. |
| 2007/0178450 A1 | 8/2007 | Wheeler et al. |
| 2007/0249012 A1 | 10/2007 | Lye et al. |
| 2007/0275370 A1 | 11/2007 | Madonna et al. |
| 2009/0208996 A1 | 8/2009 | Kadurugamuwa et al. |
| 2009/0246752 A1 | 10/2009 | Voorhees et al. |
| 2009/0258341 A1 | 10/2009 | Voorhees et al. |
| 2009/0286225 A1 | 11/2009 | Wheeler et al. |
| 2009/0286232 A1 | 11/2009 | Smith et al. |

FOREIGN PATENT DOCUMENTS

| | | |
|---|---|---|
| EP | 0228975 | 7/1987 |
| EP | 0439354 A2 | 7/1991 |
| EP | 1300082 A2 | 4/2003 |
| WO | WO 85/04189 | 9/1985 |
| WO | WO 88/04326 | 6/1988 |
| WO | WO 92/02633 | 9/1992 |
| WO | WO 93/11161 | 6/1993 |
| WO | WO 93/17129 A1 | 9/1993 |
| WO | WO 94/06931 | 3/1994 |
| WO | WO 94/13804 | 6/1994 |
| WO | WO 95/05483 A1 | 2/1995 |
| WO | WO 98/18962 A1 | 5/1998 |
| WO | WO 00/10013 | 2/2000 |
| WO | WO 01/25395 | 4/2001 |
| WO | WO 02/006117 A1 | 8/2002 |
| WO | WO 03/087772 A2 | 10/2003 |
| WO | WO 03/087772 A3 | 10/2003 |
| WO | WO 2006/012371 | 2/2006 |
| WO | WO 2006/083292 | 8/2006 |
| WO | WO 2006/105504 | 10/2006 |
| WO | WO 2008/064241 | 5/2008 |

OTHER PUBLICATIONS

Basile et al., "Pathogenic Bacteria: Their Detection and Differentiation by Rapid Lipid Profiling with Pyrolysis Mass Spectrometry," Tends in Analytical Chemistry, vol. 00, No. 0, pp. 1-15, 1997, Elsevier Science B.V., The Netherlands.
Basile et al., "Direct Mass Spectrometric Analysis of in Situ Termally Hydrolyzed and Methylated Lipids from Whole Bacterial Cells," submitted to Analytical Chemistry, 34 pages, at least as early as Apr. 12, 2002.
Beverly et al., "A Rapid Approach for the Detection of Dipicolinic Acid in Bacterial Spores Using Pyrolysis/Mass Spectrometry," Rapid Communications in Mass Spectrometry, vol. 10, pp. 455-458, 1996.
Bird et al., "Single-Chain Antigen-Binding Proteins," Science, 1988, vol. 242, pp. 423-426.
Bordner et al., "Microbiological Methods for Monitoring the Environment—Water and Wastes," Dec. 1978, prepared in part under EPA Contract No. 68-03-0431, Environmental Monitoring and Support Laboratory, Office of Research and Development, USEPA, pp. i-xvi, 1-338, Cincinnati, Ohio.
Brockman et al., "Probe-Immobilized Affinity Chromatography/Mass Spectrometry", Analytical Chemistry, vol. 67, No. 24, pp. 4581-4585, Dec. 15, 1995, American Chemical Society, USA.
Bundy et al., "Lectin and Carbohydrate Affinity Caputre Surfaces for Mass Spectrometric Analysis of Microorganisms", Analytical Chemistry, vol. 73, No. 4, pp. 751-575, Feb. 15, 2001, American Chemical Society, USA.
Cairns et al., "Quantitive Models of In Vitro Bacteriophage—Host Dynamics and Their Application to Phage Therapy," PLos Pathogens, 2009, vol. 5, No. 1, pp. 1-10.
Cardullo, "Nonradioactive Fluorescence Resonance Energy Transfer," Nonradioactive Labeling and Detection of Biomolecules, C. Kessler, Editor, Springer-Verlag, New York, 1992, pp. 414-423.
Carter, "Potent antibody therapeutics by design," Nature Reviews Immunology, 2006, vol. 6, pp. 343-357.
Casini et al., "In vitro papillomavirus capsid assembly analyzed by light scattering," Virology, 2004, vol. 325, pp. 320-327.
Chatterjee et al. "A High Yielding Mutant of Mycobacteriophage L1 and Its Application as a Diagnostic Tool", FEMS Microbiology Letters, vol. 188, pp. 47-53, 2000.
Cluett et al., "The Envelope of Vaccinia Virus Reveals an Unusual Phospholipid in Golgi Complex Membranes," Journal of Cell Science, 109, pp. 2121-2131, 1996, Great Britain.
Crews et al., "Lipids Are Major Components of Human Immunodeficiency Virus: Modification of HIV Lipid Composistion, Membrane Organization, and Protein Conformation by AL-721," Drug Development Research 14:31-44, 1988.
Cudjoe et al., "Immunomagnetic Separation of Salmonella from Foods and Their Detection Using Immunomagnetic Particle (IMP)-ELISA," International Journal of Food Microbiology, Sep. 1995, pp. 11-25, vol. 27, No. 1, Elsevier Science, The Netherlands.
Dabrowska et al., "The effect of bacteriophages T4 and HAP1 on in vitro melanoma migration," BMC Microbiol., 2009, vol. 9, pp. 9-13.
Deluca et al., Pyrolysis-Mass Spectrometry Methodology Applied to Southeasst Asian Environmental Samples for Differentiating Digested and Undigested Pollens, Analytical Chemistry, vol. 58, 2439-2442, 1986.
Deluca et al., "Direct Analysis of Bacterial Fatty Acids by Curie-Point Pyrolysis Tandem Mass Spectrometry," Analytical Chemical Society, vol. 62, No. 14, pp. 1465-1472, 1990.
Deluca et al., "Direct Analysis of Bacterial Glycerides by Curie-Point Pyrolysis-Mass Spectrometry," Journal of Analytical and Applied Pyrolysis, vol. 23, pp. 1-14, 1992, Elsevier Science Publishers B.V., The Netherlands.
Dickinson et al., "New and Improved Strategies for the Rapid Detection and Differential Identification of Microbial Spores Using MALDI-TOFMS," Proceedings of the 50th ASMS Conference on Mass Spectrometry and Allied Topics, Orlando, Florida, 2 pages; Jun. 2-6, 2002.
Dictionary.com, "Microorganism," 2009, updated, //dictionary.reference.com/browse/microorganism, pp. 1-3.
Dubow, "Bacterial Identification—Use of Phages," section in Encyclopedia Virology, 2nd Edition, R.G. Webster and A. Granoff (eds.), pp. 137-139, 1999, Academic Press, San Diego, California.
Dziadkowiec et al., "The Detection of Salmonella in Skimmed Milk Powder Enrichments Using Conventional Methods and Immunomagnetic Separation," Letters in Applied Microbiology, 1995, pp. 361-364, vol. 20, The Society for Applied Bacteriology, Blackwell Science, UK.
Ember, "Chemical Warfare Agent Detectors Probe the Fogs of War," C&EN, pp. 26-32, Aug. 1, 1994.
Favrin et al., "Development and Optimization of a Novel Immunomagnetic Separation-Bacteriophage Assay for Detection of Salmonella enterica Serovar Enteritidis in Broth," Applied and Environmental Microbiology, Jan. 2001, pp. 217-224, vol. 67, No. 1, American Society for Microbiology, Washington, D.C.
Fines et al., "Activity of linezolid against Gram-positive cocci possessing genes conferrring resistance to protein synthesis inhibitors," J. Antimicrob. Chemoth., 2000, vol. 45, pp. 797-802.
Franz, et al., "Clinical Recognition and Management of Patients Exposed to Biological Warfare Agents," JAMA, vol. 278, No. 5, pp. 399-411, Aug. 6, 1997, USA.
Gantt et al., "Use of an Internal Control for Matrix-Assisted Laser Desorption/Ionization Time-of-Flight Mass Spectrometry Analysis of Bacteria", J Am Soc Mass Spectrom, 1999, pp. 1131-1137, vol. 10, American Society for Mass Spectrometry, Elsevier Science, The Netherlands.
Garcia, et al., "The Genome Sequence of Yersinia pestis Bacteriophage ΦA1122 Reveals an Intimate History with the Coliphage T3 and T7 Genomes," Journal of Bacteriology, Sep. 2003, vol. 185, No. 17, pp. 5248-5262.
Girault et al., "Coupling of MALDI-TOF Mass Analysis to the Separation of Biotinylated Peptides by Magnetic Streptavidin Beads,"

(56) References Cited

OTHER PUBLICATIONS

Analytical Chemistry, vol. 68, No. 13, pp. 2122-2126, Jul. 1, 1996, American Chemical Society, USA.

Goodacre et al., "Rapid Identification Using Pyrolysis Mass Spectrometry and Artificial Neural Networks of *Propionibacterium Acnes* Isolated from Dogs," Journal of Applied Bacteriology, vol. 76, pp. 124-134, 1994.

Goodridge et al., "Development and Characterization of a Fluorescent-Bacteriophage Assay for Detection of *Escherichia coli* O157:H7," *Applied and Environmental Microbiology*, Apr. 1999, vol. 65, No. 4, pp. 1397-1404.

Goodridge et al., "The use of a fluorescent bacteriophage assay for detection of *Escherichia coli* O157:H7 in inoculated ground beef and raw milk," *International Journal of Food Microbiology*, 1999, vol. 47, pp. 43-50.

Grant et al., "Isolation of *Mycobacaterium paratuberculosis* from Milk by Immunomagnetic Separation," *Applied and Environmental Microbiology*, vol. 64, No. 9, pp. 3153-3158, Sep. 1998, American Society for Microbiology, USA.

Gross et al., "Mass Spectral Studies of Probe Pyrolysis Products of Intact Oligoribonucleotides," Nucleic Acids Research, vol. 5, No. 8, pp. 2695-2704, Aug. 1978, Department of Chemistry, University of Nebraska, Lincoln, Nebraska.

Hahner et al., "Matrix-Assisted Laser Desorption/Ionization Mass Spectrometry (MALDI) of Endonuclease Digests of RHA," Nucleic Acids Research, vol. 25, No. 10, pp. 1957-1964, 1997, Oxford University Press, UK.

Haynes et al., "Surface Enhanced Raman Spectroscopy," *Anal. Chem.*, 2005, pp. 339A-346A.

Heid, et al., "Real time quantitative PCR," *Genome Research*, Oct. 1996, vol. 6, No. 10, pp. 986-994.

Hendricker, "An Investigation into the Curie-point Pyrolysis-Mass Spectrometry of Glycyl Dipeptides," Journal of Analytical and Applied Pyrolysis, vol. 36, pp. 51-70, 1996.

Heylin, "The Chemicals of War," 1 page, C&EN, Mar. 9, 1998.

Higgins et al., "Competitive Oligonucleotide Single-Base Extension Combined with Mass Spectrometric Detection for Mutation Screening," BioTechniques, vol. 23, No. 4, pp. 710-714, Oct. 1997, Eaton Publishing Co., USA.

Hirsch, et al., "Rapid Detection of *Salmonella* spp. By Using Felix-O1 Bacteriophage and High-Performance Liquid Chromatography," Applied and Environmental Microbiology, vol. 45, No. 1, pp. 260-264, Jan. 1993, American Society for Microbiology, Washington, D.C.

Holland et al.,"Rapid Identification of Intact Whole Bacteria Based on Spectral Patterns Using Matrix-Assisted Laser Desorption/Ionization with Time-of-Flight Massd Spectrometry," Rapid Communications in Mass Spectrometry, vol. 10, pp. 1227-1232, 1996.

Holliger et al., "Diabodies: Small bivalent and bispecific antibody fragments," *Proc. Natl. Acad. Sci. U.S.A.*, 1993, vol. 90, pp. 6444-6448.

Holliger et al., "Engineered antibody fragments and the rise of single domains," Nature Biotechnology, 2005, vol. 23, No. 9, pp. 1126-1136.

Holmes et al., "Coronaviridae: The Viruses and Their Replication," Fundamental Virology, Third Edition, B.N. Fields et al. (eds.), pp. 541-559, 1996, Lippincott-Raven Publishers, Philadelphia.

Huang et al., "Interplay Between Lipids and Viral Glycoproteins During Hemolysis and Fusion by Influenza Virus," The Journal of Biological Chemistry, vol. 261, No. 28, pp. 12911-12914, 1986.

Huston et al., "Protein engineering of antibody binding sites: Recovery of specific activity in an anti-digoxin single-chain Fv analogue produced in *Escherichia coli,*" *Proc. Natl. Acad. Sci. U.S.A.*, 1988, vol. 85, pp. 5879-5883.

Jenison et al., "Silicon-Based Biosensors for Rapid Detection of Protein or Nucleic Acid Targets," Clinical Chemistry, vol. 47, No. 10, pp. 1894-1900, Oct. 2001, American Association for Clinical Chemistry, Inc.

Jenison et al., "Thin Film Biosensor for Rapid Detection of mecA from Methicillin-resistant *Staphylococcus aureus*," Clinical Chemistry, vol. 46, No. 9, pp. 1501-1504, Sep. 2000, American Association for Clinical Chemistry, Inc.

Kermasha et al., "Comparative High-Performance Liquid Chromatographic Analyses of Cholesterol and Its Oxidation Products Using Diode-Array Ultraviolet and Laser Light-Scattering Detection," Journal of Chromatography A, vol. 685, pp. 229-235, 1994.

Kingsbury et al, "Rapid Detection and Identification of Infectious Agents," pp. i-xii, 1-296, Academic Press, Inc., Orlando, Florida 1985.

Kodikara et al., "Near On-Line Detection of Enteric Bacteria Using Lux Recombinant Bacteriophage," FEMS Microbiology Letter, vol. 83, pp. 261-265, 1991, Federation of European Microbiological Societies, Elsevier, The Netherlands.

Krishnamurthy et al., "Rapid Identification of Bacteria by Direct Matrix-assisted Laser Desorption/Ionization Mass Spectrometric Analysis of Whole Cells," *Rapid Communications in Mass Spectrometry*, 1966, vol. 10, pp. 1992-1996.

Lamoureux et al., "Detection of *Campylobacter jejuni* in Food and Poultry Viscera Using Immunomagnetic Separation and Microtitre Hybridization", Journal of Applied Microbiology, vol. 83, pp. 641-651, 1997, The Society for Applied Bacateriology, UK.

Le Cacheux et al., "Quantitative Analysis of Cholesterol and Cholesterol Ester Mixtures Using Near-Infared Fourier Transform Raman Spectroscopy," Applied Spectroscopy, vol. 50, No. 10, pp. 1253-1257, 1996.

Lech, et al., "Section III Vectors Derived from Lambda and Related Bacteriophages," *Current Protocols in Molecular Biology*, Frederick M. Ausubel, et al. (Editor), ISBN: 978-0-471-50338-5, 1987, 34 pages.

Lynn et al., "Identification of Enterobacteriaceae Bacteria by Direct Matrix-assisted Laser Desorption/Ionization Mass Spectrometric Analysis of Whole Cells," vol. 13, No. 20, pp. 2022-2027, 1999, John Wiley & Sons, Ltd., Hoboken USA.

Madonna, et al., "On-probe sample pretreatment for the detection of proteins above 15 Kda from whole cell bacteria by matrix-assisted laser desorption/ionization time-of-flight mass spectrometry," *Rapid Communications in Mass Spectrometry*, 2000, vol. 14, p. 2220-2229.

Madonna et al., "Detection of Bacteria from Biological Mixtures Using Immunomagnetic Separation Combined with Matrix-Assisted Laser Desorption/Ionization Time-of-Flight Mass Spectrometry," *Rapid Communications in Mass Spectrometry*, vol. 15, No. 13, pp. 1068-1074, Jun. 6, 2001, John Wiley & Sons, Ltd., Hoboken, USA.

Madonna et al., "Detection of *Escherichia coli* Using Immunomagnetic Separation and Bacteriophage Amplification Coupled with Matrix-assisted laser Desorption/Ionization Time-of-flight Mass Spectrometry," Rapid communications in Mass Spectrometry, published online Dec. 24, 2002 in Wiley InterScience (www.interscience.wiley.com), pp. 257-263, vol. 17, John Wiley & Sons, Ltd.

Madonna et al., "Isolation and Enrichment of *Salmonella* on Immunomagnetic Beads Prior to Detection by MALDI-TOFMS" (extended abstract), *49th ASMS Conference on Mass Spectrometry and Allied Topics*, May 27-31, 2001, Session Code: MPI, Slot: 204, 1 page, USA.

Madonna et al., "Investigation of Cell Culture Media Infected with Viruses by Pyrolysis Mass Spectrometry: Implications for Bioaerosol Detection," American Society for Mass Spectrometry, vol. 10, No. 6, pp. 502-511 Jun. 1999.

Madonna, et al., "Investigation of Viruses Using Pyrolysis Mass Spectrometry," [appears to be an internal power point presentation], 1999 10(6):502-511. J of Am Soc.M.

Mandeville et al., "Diagnostic and Therapeutic Applications of Lytic Phages," *Anal. Lett.*, 2003, vol. 36, No. 15, pp. 3241-3259.

Mansfield et al., "Immunomagnetic Separation as an Alternative to Enrichmnet Broths for *Salmonella* Detection", Letters in Applied Microbiology, vol. 16, pp. 122-125, 1993.

Marple et al., "Aerosol Sample Acquisition for Chemical and Biological Agent Detection," Abstract, Report No. ARO-25616,1-CHS, Army Research Office, Dec. 1, 1989.

Meuzelaar et al., "Characterization of Leukemic and Normal White Blood Cells by Curie-Point Pyrolysis-Mass Spectrometry. Bio-

(56) References Cited

OTHER PUBLICATIONS chemical Interpretation of Some of the Differences in the Pyrolysis Patterns," Journal of Analytical and Applied Pyrolysis, vol. 3, pp. 111-129, 1981.

Munoz-Barroso et al., "Dynamic Properties of Newcastle Disease Virus Envelope and Their Relations with Viral Hemagglutinin-Neuraminidase Membrane Glycoprotein," Biochimica et Biophysica Acta, vol. 1327, pp. 17-31, 1997.

Nakamura et al., "A Visualizatoin Method of Filamentous Phage Infection and Phage-Derived Proteins in *Escherichia coli* Using Biotinylated Phages," Biophysical and Biophysical Research Communications, vol. 289, No. 1, pp. 252-256 Nov. 2001.

Nelson et al., "Mass Spectrometric Immunoassay", Analytical Chemistry, vol. 67, No. 7, pp. 1153-1158, Apr. 1, 1995, American Chemical Society, USA.

Nyiendo, et al., "Preparation and Storage of High-Titer Lactic Streptococcus Bacteriophages," Applied Microbioilogy, vol. 27, No. 1, pp. 72-77, Jan. 1974, American Society for Microbiology.

Okrend et al., "Isolation of *Escherichia coli* O157:H7 Using O157 Specific Antibody Coated Magnetic Beads", *Journal of Food Protection*, Mar. 1992, pp. 214-217, 55, International Association of Milk, Food and Environmental Sanitarians.

Olsvik et al., "Magnetic Separation Techniques in Diagnostic Microbiology," Clinical Microbiology Reviews, vol. 7 No. 1, pp. 43-54, Jan. 1994.

Ostlund et al., "Quantification of Cholesterol Tracers by Gas Chromotography-Negative Ion Chemical Ionization Mass Spectrometry," Journal of Mass Spectrometry, 31:1291-1296, 1996.

Patzer et al., "Lipid Organization of the Membrane of Vesicular Stomatitis Virus," The Journal of Biological Chemistry, vol. 253, No. 13, pp. 4544-4550, Jul. 1978.

Pugh et al., "A Complete Protocol Using Conductance for Rapid Detection of *Salmonellas* in Confectionary Materials," Letters in Applied Microbiology, 1988, p. 23-27, vol. 7, The Society for Applied Microbiology, Blackwell Science, UK.

Pyle et al., "Sensitive Detection of *Escherichia coli* O157:H7 in Food and Water by Immunomagnetic Separation and Solid-Phase Laser Cytometry", Applied and Environmental Microbiology, May 1999, pp. 1966-1972, vol. 65, No. 5, American Society for Microbiology, Washington, D.C.

Rowe et al., "An Array Immunosensor for Simultaneous Detection of Clinical Analytes", *Analytical Chemistry*, Jan. 15, 1999, 71-#2, American Chemical Society, USA.

Ryzhov et al., "Characterization of the Protein Subset Desorbed by MALDI from Whole Bacterial Cells," Analytical Chemistry, Feb. 15, 2001, pp. 746-750, vol. 73, No. 4, American Chemical Society, Washington, D.C.

Sambrook et al., *Molecular Cloning: A Laboratory Manual*, Second Edition, 1889, Cold Spring Harbor Laboratory Press, 27 pages (Title page and Table of Contents).

Sanderson, et al., "Surface Sampling Methods for *Bacillus anthracis* Spore Contamination," Emerging Infectious Diseases, vol. 8, No. 10, pp. 1145-1151, Oct. 2002.

Schlesinger, "Detecting Battlefield Toxins," Popular Science, 2 pages Oct. 1998.

Siuzdak, "Probing Viruses with Mass Spectrometry," *Journal of Mass Spectrometry*, vol. 33, pp. 203-211, 1998, John Wiley & Sons Ltd.

Skjerve et al., "Detection of *Listeria monocytogenes* in Foods by Immunomagnetic Separation," Applied and Environmental Microbiology, Nov. 1990, pp. 3478-3481, vol. 56, No. 11, American Society for Microbiology, Washington, DC.

Stankiewicz et al., "Assessment of Bog-body Tissue Preservation by Pyrolysis-Gas Chromatography/Mass Spectrometry," Rapid Communications in Mass Spectrometry, vol. 11, pp. 1884-1890, 1997.

Stewart et al., "The specific and sensitive detection of bacterial pathogens within 4 h using bacteriophage amplification," Journal of Applied Microbiology, vol. 84, pp. 777-783, 1998, The Society for Applied Microbiology, Blackwell Science, U.K.

Stewart, "In vivo bioluminescence: new potentials for microbiology," Letters in Applied Microbiology, vol. 10, pp. 1-8, 1990, The Society for Applied Microbiology, Blackwell Science, UK.

Strauss, et al., "Purification and Properties of Bacteriophage MS2 and of its Ribonucleic Acid," J. Mol. Biol., vol. 7, pp. 43-54, 1963, Elsevier Science, The Netherlands.

Sun et al., Use of Bioluminescent *Salmonella* for Assessing the Efficiency of Constructed Phage-Based Biosorbent, *Journal of Industrial Microbiology & Biotechnology*, 2000, vol. 25, pp. 273-275, Nature Publishing Group.

Sun et al., "Use of Bioluminescent *Salmonella* for Assessing the Efficiency of Constructed Phage-Based Biosorbent," Journal of Industrial Microbiology & Biotechnology, vol. 27, No. 2, pp. 126-128, Aug. 2001.

Tan et al., "Rapid Simultaneous Detection of Two Orchid Viruses Using LC- and/or MALDI-mass Spectrometry," *Journal of Virological Methods*, vol. 85, pp. 93-99, 2000, Elsevier Science B.V., The Netherlands.

Tas et al., "Characterization of Virus Infected Cell Cultures by Pyrolysis/Direct Chemical Ionization Mass Spectrometry," Biomedical and Environmental Mass Spectrometry, vol. 18, pp. 757-760, 1989.

Thomas et al., "Viral Characterization by Direct Analysis of Capsid Proteins," Analytical Chemistry, vol. 70, No. 18, pp. 3863-3867, Sep. 15, 1998.

Tomlinson et al., "Methods for Generating Multivalent and Bispecific Antibody Fragments," *Methods Enzymol.*, 2000, vol. 326, pp. 461-479.

Tremblay, "DARPA Expands R&D on Biowarfare Defense Tools," 1 page, C&EN, Feb. 16, 1998.

Van De Plas et al., "Colloidal Gold as a Marker in Molecular Biology: The Use of Ultra-Small Gold Particles," *Nonradioactive Labeling and Detection of Biomolecules*, C. Kessler, Editor, Spring-Verlag, New York, 1992, pp. 116-126.

Van Der Wolf et al., "Immunomagnetic separation of *Erwinia caratovora* subsp. Astroseptica from potato peel extracts to improve detection sensitivity on a crystal violet pectate medium or by PCR," Journal of Applied Bacteriology, vol. 80, pp. 487-495, May 1996, Blackwell Science, UK.

Van Hoeven et al., "Studies on Plasma Membranes," Biochimica et Biophysica Acta, vol. 380, pp. 1-11, 1975, Elesevier Scientific Publication Company, The Netherlands.

Voorhees et al., "An Investigation of the Pyrolysis of Oligopeptides by Curie-point Pyrolysis-tandem Mass Spectrometry," Journal of Analytical and Applied Pyrolysis, vol. 30, pp. 1-16, 1994, Elsevier Science B.V., The Netherlands.

Wang et al., "Investigation of Spectral Reproducibility in Direct Analysis of Bacteria Proteins by Matrix-Assisted Laser Desorption/Ionization Time-of-Fight Mass Spectrometry," Rapid Communications in Mass Spectrometry, vol. 12, pp. 456-464, 1998, John Wiley & Sons, Ltd., Hoboken, USA.

Ward et al., "Binding activities of a repertoire of single immunoglobulin variable domains secreted from *Escherichia coil*," *Nature*, 1989, vol. 341, pp. 544-546.

Windig et al., "Control of the Absence of Deae-Polysaccharides in Deae-Sephadex Purified Poliovirus Suspensions by Pryolysis Mass Spectrometry," Develop. Biol Standard, vol. 47, pp. 169-177, 1981.

Wu et al., "A hairpin aptamer-based electrochemical biosensing platform for the sensitive detection of proteins," *Biomaterials*, 2009, vol. 30, pp. 2950-2955.

Wyatt et al., "Immunoassays for Food-poisoning Bacteria and Bacterial Toxins," Nov. 1992, pp. i-xiii, 1-129, James & James (Science Publishers) Ltd. and Chapman & Hall, London, Great Britain.

Yates et al., "Method to Compare Collison-Induced Dissociation Spectra of Peptides: Potential for Library Searching and Subtractive Analysis," Analytical Chemisry, vol. 70, pp. 3557-3565, 1998.

(56) References Cited

OTHER PUBLICATIONS

Yu et al, "Immunomagnetic-Electrochemiluminescent Detection of *Escherichia coli* O157 and *Salmonella typhimurium* in Foods and Environmental Water Samples," Applied and Environmental Microbiology, vol. 62, No. 2, pp. 587-592, Feb. 1996, American Society for Microbiology, Washington, D.C.

In the US Patent and Trademark Office, U.S. Appl. No. 10/249,452, Non-Final Office Action dated Feb. 23, 2005, 12 pages; and corresponding response dated Aug. 26, 2005, 17 pages.

In the US Patent and Trademark Office, U.S. Appl. No. 10/249,452, Non-Final Office Action dated Feb. 7, 2006, 9 pages; and corresponding response dated Aug. 7, 2006, 7 pages, and supplemental response dated Aug. 30, 2006, 6 pages.

In the US Patent and Trademark Office, U.S. Appl. No. 10/823,294, Final Office Action dated Dec. 3, 2007, 14 pages; and corresponding response and RCE dated Mar. 3, 2008, 14 pages.

In the US Patent and Trademark Office, U.S. Appl. No. 10/893,294, Non-Final Office Action dated Apr. 25, 2008, 11 pages; and corresponding response dated Aug. 25, 2008, 5 pages.

In the US Patent and Trademark Office, U.S. Appl. No. 10/823,294, Non-Final office Action dated Jul. 23, 2007, 20 pages; and corresponding response dated Nov. 21, 2007, 24 pages.

In the US Patent and Trademark Office, U.S. Appl. No. 10/823,294, Non-Final Office Action dated Sep. 30, 2008, 8 pages; no response made.

* cited by examiner

DETECTION OF PHAGE AMPLIFICATION BY SERS NANOPARTICLES

CROSS REFERENCE TO RELATED APPLICATION

This application claims the benefit of priority under 35 USC §119(e) to U.S. patent application Ser. No. 61/020,454, entitled "Detection of Phage Amplification by SERS Nanoparticles" and filed Jan. 11, 2008, the entirety of which is hereby incorporated by reference.

FEDERALLY SPONSORED RESEARCH CLAUSE

The U.S. Government has a paid-up license in this invention and the right in limited circumstances to require the patent owner to license others on reasonable terms as provided by the terms of Grant No. W81XWH-07-C-0061 awarded by the United States Army Medical Research Center.

BACKGROUND

Substrate based assays are typically relied upon to detect the presence of bacterial and other pathogens. Such standard microbiological methods for detecting microorganisms do not require expensive equipment or lab facilities, are generally easy to carry out, and provide high levels of selectivity and sensitivity. However, such methods are slow, as they require a pure culture of the target organism, which can take a day or more to cultivate or grow.

Certain molecular biology techniques are alternatives to the standard microbiological tests. For example, serological methods have gained wide acceptance. Such techniques do not require cultivation of the biological sample, thus reducing the time necessary to perform the test. Other techniques can utilize phage, or bacteriophage in the case of bacteria, to infect the target organism. The infected bacterium can subsequently emit light or release certain nucleotides or release progeny phage. However, these tests cannot capitalize on the ability to detect progeny phage. Further, the tests are time consuming to perform and do not achieve the same levels of selectivity and sensitivity. They are also more expensive and require a more highly trained lab technician than do the substrate based assays.

Some optical based detection methods utilize optical tags, such that the tagged organism is illuminated or visualized with a spectrometer. The optical-based detection methods can rely on beads or other particles that produce a signal. However, these tests do not attempt to detect progeny phage.

Thus, a method for detecting progeny phage that utilizes an optical-based detection method combined with the sensitivity, selectivity and lower cost of the substrate based assay and the quick results of a molecular biology technique is needed. This and other needs are addressed by the present invention.

SUMMARY

The present disclosure provides a phage specific antibody presenting particle, devices, and methods related to detection of phage amplification. The particle includes a metal core, enveloped by a reporter molecule coating (also referred to as a "coating" or a "reporter molecule"). A glass coating is attached to the reporter molecule coating. Phage specific antibodies are attached to the glass coating. Following phage amplification, the phage specific antibody presenting particle can be introduced to the amplified phage either before or after the amplified phage is immobilized on a solid surface of, for example, a lateral flow device or a stationary phase, to form a particle-phage-immobilized antibody conjugate. The particle of the particle-phage-immobilized antibody conjugate can be detected by a Raman spectrometer, preferably a surface-enhanced Raman scattering (SERS) spectrometer, thus detecting or indicating the presence of progeny phage. The detection of phage amplification, in turn, can indicate the presence of a target microscopic living organism (microorganism), such as a bacterium or fungi, in a sample. In various aspects, the particle, devices, and methods offer a combination of specificity, sensitivity, simplicity, speed, and cost effectiveness.

While multiple embodiments are disclosed, still other embodiments of the invention will become apparent to those skilled in the art from the following Detailed Description, which shows and describes illustrative embodiments of the invention. As will be realized, the invention is capable of modifications in various aspects, all without departing from the spirit and scope of the invention. Accordingly, the drawings and detailed description are to be regarded as illustrative in nature and not restrictive.

DETAILED DESCRIPTION

Figure 1:
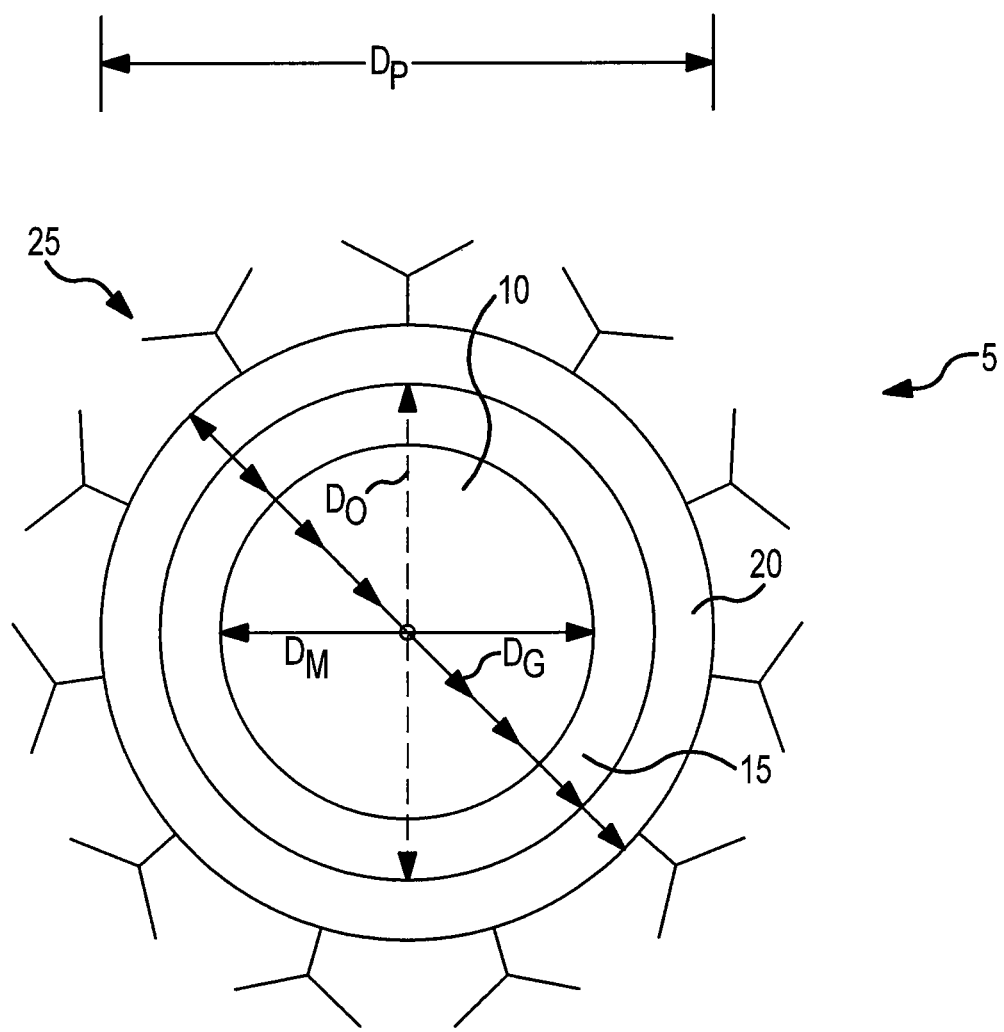
FIG. 1 depicts a phage specific antibody-presenting particle for detecting phage, including a metal core and phage specific antibodies attached to an external surface of the particle.

The present disclosure provides a phage specific antibody presenting particle, devices and methods related to detection of phage amplification. The detection of phage amplification can indicate the presence of target microscopic living organism (microorganism), such as a bacterium or fungi, in a sample. In various embodiments, the particle, devices and methods offer specificity, sensitivity, simplicity, speed and cost effectiveness.

The particle includes a metal core, enveloped by a reporter molecule coating. The reporter molecule coating is attached to a glass coating. Phage specific antibodies are attached to the glass coating. After a phage amplification process, the phage specific antibody presenting particle is introduced to the amplified phage either before or after the amplified phage is immobilized on a solid surface to form an immobilized surface-phage-antibody conjugate. In various embodiments, the solid surface can be a lateral flow device or a stationary phase, to form an immobilized particle-phage antibody conjugate. The particle of the particle-phage antibody conjugate can be detected by a Raman spectrometer, preferably using SERS, thus detecting or indicating the presence of progeny phage. In various embodiments, the particle can have properties and components as discussed in U.S. Pat. Nos. 6,514,778 and 7,195,778, which are incorporated herein by reference in their entirety.

As used herein, "disposed on" and "attached to" are used interchangeably to include covalent and non-covalent attachment.

As used herein, "operably associated with", "operatively connected," and "operably connected" are references to a joinder of elements, are used interchangeably, and are to be construed broadly and may include intermediate members between a connection of elements and relative movement between elements. As such, the terms do not necessarily infer that two elements are directly connected and in fixed relation to each other.

The reporter molecule coating is selected to produce a characteristic Raman spectrum. The characteristic Raman spectrum is enhanced by some of the components of the particle. In certain aspects, the reporter molecule coating is a spectroscopy-active layer. When excited, the reporter molecule coating exhibits a simple Raman spectrum.

The Raman spectrum is enhanced when the reporter molecule coating is in close proximity to a metal surface, such as the metal core. Such enhancement is known as surface-enhanced Raman scattering (SERS). SERS permits detection of molecules attached to the surface of a particle. Thus, a SERS particle acts as an optical tag. Further, because a single Raman spectrum can show the characteristic Raman spectra of each reporter molecule coating, multiple particles with different reporter molecule coatings can be distinguished in this multiplexed format.

The ability to detect progeny phage in a simple, efficient, sensitive and cost-effective manner is advantageous for many applications, including, but not limited to, human clinical and field diagnostics, environmental testing, food pathogen detection, veterinary diagnostics, and biowarfare detection. Further, phage amplification detection with, for example, a lateral flow device, shows feasibility in detecting low concentrations of bacteria and fungi. In some embodiments, the detection limit may be at or below approximately 20 fM. In various embodiments, the detection limit may be 20 fM, 18 fM, 16 fM, 14 fM, 12 fM, or 10 fM.

For a discussion of an embodiment of a phage specific antibody presenting particle, reference is made to FIG. 1. FIG. 1 depicts one embodiment of a phage specific antibody-presenting particle 5 for detecting phage, including a metal core 10 and phage specific antibodies 25 attached to an external surface of the particle 5. As shown in FIG. 1, the particle 5 includes a metal core 10, a reporter molecule coating or simply, a reporter molecule 15, a glass coating 20 and phage specific antibodies 25. In one embodiment, the particle 5 has a metal core 10, with a reporter molecule coating 15 attached to or in close proximity to the particle core 10 and a glass coating 20 attached to the surface of the reporter molecule coating 15, and phage specific antibodies 25 attached to the surface of the glass coating 20. The diameter $D_P$ of the particle 5 is between approximately 21 nm and approximately 240 nm. The diameter of the particle 5 may be greater than 240 nm or less than 21 nm depending upon the diameter of the core 10, the diameter of the glass coating 20 and the diameter of the reporter molecule coating 15, as discussed in more detail below.

As illustrated in FIG. 1, the particle 5 includes a metal core 10. The metal core can be any metallic composition that is known in the art to have electromagnetic or chemical enhancement properties. In one embodiment, the metal core 10 is gold (Au). In an alternative embodiment, the metal core 10 is silver(Ag). The metal core 10 can also be copper(Cu), sodium(Na), potassium(K), chromium(Cr), aluminum(Al), lithium(Li), or a metal alloy. In other embodiments, the metal core can be pure metal or a metal alloy and can be overlaid with at least one metal shell, such as a core-shell particle comprised of Au/AuS.

The metal shell can be chosen so as to maximize the Raman signal's intensity from the reporter molecule coating. The metal core can have any shape, including a sphere, ellipsoid, or cylinder. In cases where the metal core is a sphere, diameter $D_M$ of the spherical metal core 10 is between approximately 20 nm and approximately 200 nm. In an alternative embodiment, the diameter of the core 10 may be between approximately 40 nm and approximately 100 nm. In various permutations, the core can have a diameter of greater than 10 nm, 20 nm, 30 nm, 40 nm, 50 nm ,60 nm, 70 nm, or 80 nm, and/or less than 300 nm, 280 nm, 260 nm, 240 nm, 220 nm, 200 nm, 190 nm, 180 nm, 170 nm, 160 nm, 150 nm, 140 nm, 130 nm, 120 nm, 110 nm, or 100 nm. Alternatively, the metal core can be an oblate or prolate spheroid in which at least one diameter is as described for spherical embodiments above.

Referring again to FIG. 1, the reporter molecule coating 15 is attached to the metal core 10. The reporter molecule coating 15 is a spectroscopy-active layer and exhibits a simple Raman spectrum. The Raman spectrum is enhanced when the reporter molecule coating 15 is in close proximity to a metal surface, such as the metal core 10. The diameter $D_O$ of the reporter molecule coating 15 is determined by the difference between the diameter $D_G$ of the glass coating and the diameter $D_M$ of the metal core. A person skilled in the art will recognize that the reporter molecule coating 15 can be any type of molecule with a measurable SERS spectrum, and can be a single layer or multi-layered. However, a reporter molecule coating without measurable Raman activity can also be used. A measurable spectrum is one in which the presence of the reporter molecule coating, and/or possibly the core, can be detected and recognized as a characteristic of the particular reporter molecule coating. Generally, suitable Raman-active reporter molecule coatings have (i) strong Raman activity thus minimizing the number of particles necessary to provide a detectable signal and (ii) a simple Raman spectrum which permits the use of multiple different particles which can be distinguished even if used simultaneously.

The reporter molecule coating can be a polymer to which a single or multiple Raman-active molecules are attached. Alternatively, the reporter molecule coating can be a single type of reporter molecule coating or many different types of reporter molecule coatings. Reporter molecule coatings can include one or more molecular species (positively or negatively charged, neutral or amphoteric) or a non-molecular species such as a negatively or positively charged ion. Non-limiting examples of possible Raman-active molecules number in the millions, and include HCl, Hg, $CN^-$, dimethylformamide, diamond, charcoal, polypyrrole, oligonucleotides, rust, sulfur, carbon, citric acid and polyacrylamide. Additionally or alternatively, the reporter molecule coating can include a metal oxide.

The peaks in a single Raman spectrum are distinct and easily resolvable for each reporter molecule coating. While Raman spectrometers are used in various embodiments, any form of monochromator or spectrometer that can temporally or spatially resolve photons and any type of photon detector known in the art can be used.

Detection can be performed using visible or near-IR irradiation. Other optical detection/interrogation methods known in the art, and which can be utilized exclusively or in combination with SERS as described in the present disclosure, include: use of a resonantly-excited reporter molecule coating or surface enhanced resonance Raman scattering (SERRS), surfaced enhanced infrared absorption spectra (SEIRA), surface enhanced hyper Raman scattering (SE-HRS), as well as the resonant analogue SEHRRS.

In certain embodiments, a SER spectroscopy is used to detect the particles. SERS provides improved specificity and sensitivity over other detection techniques, including RAMAN techniques. SERS is a vibrational spectroscopy technique. Thus, a SER spectrum provides more information about molecular structure and the local environment in condensed phases than an electronic spectroscopy technique, such as, for example, fluorescence. Further, the reporter molecule coating may be on or near a noble metal, thereby providing a nonradiative pathway for decay of excited states. This quenches fluorescence interference. In particular, SERS provides enhanced detection limits. In some embodiments, the detection limit is at or below approximately 20 fM. In various embodiments, the detection limit may be 20 fM, 18 fM, 16 fM, 14 fM, 12 fM, or 10 fM.

The information obtained from Raman spectra is characteristic of the reporter molecule. Minor changes in the orientation of an adsorbate can be discerned because slight variations produce measurable shifts in the peaks of the SERS spectrum. Low frequency vibrational modes beyond the range of IR absorption spectroscopy can be observed with SERS, with instrumentation that is appropriate. In various aspects, SERS provides for improved sensitivity over conventional Raman methods by a factor of $10^3$ to $10^6$, and in some instances between approximately $10^4$ to approximately $10^{15}$. In various embodiments, reporter molecules may be selected, and SERS may be performed, as described, for example in Haynes et al., *Surface Enhanced Raman Spectroscopy*, Anal. Chem. 339A-346A (2005), incorporated herein by reference in its entirety.

Because different reporter molecule coatings produce different spectra, the system can be multiplexed. That is, a particle with a specific reporter molecule coating can be designed and used for each type of phage, thus enabling a multiplexed assay with several different phages.

As illustrated in FIG. 1, the glass coating 20 is attached to the reporter molecule coating 15. In one embodiment, the glass coating 20 can be, for example, $SiO_x$, and can be modified for operably attaching phage-specific antibodies 25. The glass coating 20 can also provide a barrier to protect or otherwise keep the surrounding solvent away from the reporter molecule coating 15. The diameter $D_G$ of the glass coating 20 is between approximately 1 nm and approximately 40 nm. In an alternative embodiment, the diameter of the glass coating 20 may be between approximately 10 nm and approximately 20 nm. The dimensions of the particles can be varied as described herein.

It can be appreciated that in alternative embodiments, the core and reporter molecule coating complex may be attached to polymers, metals, metal oxides (such as $TiO_2$ and $SnO_2$) and metal sulfides or any other material that may provide a surface for operably attaching a phage specific antibody.

Preferably, the glass coating will not have a measurable effect on the SERS activity. However, if the glass coating does have a measurable effect, it will not interfere with the SERS activity. The thickness of the glass coating can vary and the thickness can have an adverse effect on the intensity of the spectrum. That is, if the glass coating is too thick, it will be difficult to obtain an intense Raman spectrum. The intensity of the Raman scatter decreases exponentially with distance between the surface of the core and the reporter molecule coating.

As shown in FIG. 1, in one embodiment, phage specific antibodies 25 are located on an external surface of the particle 5. The phage specific antibodies 25 can be grafted or otherwise operably attached to an external surface of particle 5, i.e., onto the glass coating 20. Usage of non-specific phage antibodies increases the likelihood of cross-reactivity to other phages present in the sample. Thus, it is advantageous to use phage-specific antibodies to reduce the likelihood of cross-reactivity, thereby increasing efficiency and reliability.

Antibodies

For purposes of the present disclosure, the term "antibody" is used in the broadest sense and specifically covers monoclonal antibodies, polyclonal antibodies, multispecific antibodies, e.g., bispecific antibodies, chimeric antibodies, humanized antibodies, fully synthetic antibodies and antibody fragments so long as they exhibit the desired biologic activity, i.e., binding specificity. An antibody is a monomeric or multimeric protein comprising one or more polypeptide chains. An antibody binds specifically to an antigen and can be able to modulate the biological activity of the antigen. The term "antibody" also includes antibody fragments. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, Methods Enzymol. 326: 461-479; WO94/13804; Holliger et al., 1993, Proc. Natl. Acad. Sci. U.S.A. 90:6444-6448). In certain embodiments, antibodies are produced by recombinant DNA techniques. Other examples of antibody formats and architectures are described in Holliger & Hudson, 2006, Nature Biotechnology 23(9):1126-1136, and Carter 2006, Nature Reviews Immunology 6:343-357 and references cited therein, all expressly incorporated by reference. In additional embodiments, antibodies are produced by enzymatic or chemical cleavage of naturally occurring antibodies.

Phage

In this disclosure, the term "phage" include bacteriophage, phage, mycobacteriophage (such as for TB and paraTB), mycophage (such as for fungi), mycoplasma phage or mycoplasmal phage, and any other term that refers to a virus that can invade living bacteria, fungi, mycoplasmas, protozoa, and other microscopic living organisms and uses the host organism to replicate itself. Note that for purposes of this disclosure any phage that can specifically adsorb with a microorganism can be useful, however, for simplicity sake, the disclosure often refers to bacteriophage and bacterium.

Bacteriophage are viruses that use, for example, bacteria as a way to replicate themselves. Other phages use other organisms, such as fungi. A bacteriophage does this by attaching itself to a bacterium and injecting its DNA into that bacterium, inducing it to replicate the bacteriophage hundreds or even thousands of times. Some bacteriophage, called lytic bacteriophage, rupture the host bacterium, releasing the progeny phage into the environment to seek out other bacteria. The total incubation time for phage infection of a bacterium, phage multiplication or amplification in the bacterium, to lysing of the bacterium may take anywhere from minutes to hours, depending on the bacteriophage and bacterium in question and the environmental conditions.

Detection of phage amplification can be performed in various ways. In one embodiment, a parent phage can be amplified to create progeny phage, the progeny phage can be exposed to one or more of the particles as described above, and the particle detected by Raman spectroscopy to detect the progeny phage.

Generally, a phage that is specific to a target microorganism is introduced into a sample. The phage will infect and multiply within the microorganism if the target microorganism is present. Conditions are provided such that the phage is allowed to infect the target microorganism and multiply in the target to create a detectable amount of phage or biological substance associated with the bacteriophage in the sample. Then, the microorganism is lysed as a result of the multiplication of the phage or by actively lysing with, for example, a bacterial lysozyme, if the target is a bacterium.

Prior to a detection process, a spectrum or other baseline for the introduced phage may be established or the introduced phage and progeny phage, if any, may be identified or separated to further enhance detection. In one embodiment, the amount of introduced phage, or "parent phage", is likely below the detection limit of the phage and, if present, the progeny phage will rise above this level. In an alternative embodiment, the SERS spectrum of the phage that are introduced into the system is detected and may be used as a baseline for the phage concentration itself. In other alternative embodiments, the parent phage may be tagged. In still other alternative embodiments, the parent phage may be removed and the progeny phage detected, as described in more detail below.

SERS may be used to detect the parent phage or the progeny phage. For example, parent phage or progeny phage can be immobilized to create a particle-phage-antibody-conjugate. The reporter molecule coating will produce a Raman spectrum. A different particle is used for the progeny phage and the parent phage. Thus, if progeny phage are present, a Raman spectrum will be produced.

The sample is assayed for the phage or biological substance associated with the phage, such as with a lateral flow strip and Raman spectroscopy, preferably SERS, as described in more detail below. If phage are detected, this indicates the presence of the targeted microorganism. If no phage are detected, or an increase in the number of phage above baseline is observed, this indicates the absence of the targeted microorganism. The total incubation process of infection, replication and lysis may take only a few minutes.

In one embodiment, to detect single or multiple bacteria, one species of bacteriophage is added to a raw sample (i.e. a sample prior to the addition of phage) for each target bacterium giving a single test sample that contains all of the target bacteria and associated phages. The raw sample containing the target bacterium is generally in a liquid form but could be a mixture containing many different organic and inorganic compounds. The raw sample may be pretreated in a variety of ways to prepare it for testing. For example, the raw sample may be purified or filtered to remove unwanted components or to concentrate the target bacterium. The raw sample may be cultured in a media conducive to the incubation of the target bacterium or to induce the target bacterium into a more viable state. The raw sample may be in a relatively untreated state such as in a sputum, blood, or water sample. It should be clear to one skilled in the art that pretest sample preparation can include any suitable process and the raw sample can take many different forms.

The phage itself may be added to the sample in any suitable form. For example, the phage may be added in a dry state, or the phage may be mixed or suspended in a vial to which the raw sample is added. The phage added to the raw sample is herein referred to as the "parent phage".

A test sample comprising the raw sample and the parent phage is incubated and the parent phage infects the target bacteria by attaching themselves to cell walls of the target bacteria and injecting the viral nucleic acid to create infected bacteria. Replication of progeny phage proceeds within the host bacteria. If lytic phages are used, the host will rupture, thereby releasing progeny phage into the test sample. The progeny phage can then infect other target bacteria. If there were target bacteria in the raw sample, the test sample will contain a large number of progeny phage. An additional step can be performed whereby a suitable lysozyme is added to lyse any infected target bacteria that did not lyse naturally. The suitable lysozyme will rupture the cell walls and any progeny phage still held within the host bacteria will be released into the test sample and can now be detected.

In accordance with the present disclosure, in one embodiment, the progeny phage may then be contacted with an antibody specific to the phage. The antibody may be immobilized on a solid surface, thereby immobilizing the phage when the phage come into contact with the antibody on, for example, a lateral flow strip or other stationary phase and thereby creating an antibody-phage conjugate. The immobilized phage may then be contacted with a phage specific antibody presenting particle, and the particle(s) may bind to the antibody-phage conjugate, thereby creating an antibody-phage-particle conjugate. In an alternative embodiment, the phage specific antibody presenting particle may contact the amplified phage in solution and the phage may conjugate with the antibody on the external surface of the particle, thereby creating a particle-phage conjugate. The particle-phage conjugate may then be contacted with antibodies immobilized on a solid surface or other stationary phase, including but not limited to a lateral flow strip, lateral flow chromatography, other lateral flow device, a solid column, magnetic beads (i.e. antibodies are attached to a glass-coated magnet), and thereby creating a particle-phage-antibody conjugate.

Once the particle is bound to the phage and immobilized on the solid surface (i.e. the particle-phage-antibody conjugate), the particle can be detected based on a characteristic Raman spectrum provided by the reporter molecule coating of the particle. The concentration of the phage in the incubated test sample is higher than that of the target bacteria in the raw sample because of phage amplification. Thus, lower concentrations of bacteria can be detected where the method, device, kit or process is detecting amplified phage.

Once the phage amplification is completed and the progeny phage are introduced and subsequently conjugated to the particle and/or phage specific antibodies, the resulting conjugate can be analyzed using a lateral flow device as described in more detail below. Alternatively, as described in more detail below, the resulting conjugate can also be analyzed in a solid column or in a 96-well or other multi-well plate.

The present disclosure also provides a lateral flow device that can be used for detecting progeny phage. In some embodiments, the lateral flow device can be used for multiplexing analysis. In some embodiments, the device can be a lateral flow device comprising a particle disposed on one or more lateral flow strips.

The lateral flow device may be used to detect phage amplification. For example, in one embodiment, phage specific antibodies are located on an external surface of the particle. The particle can be introduced to a sample that can include progeny phage. If progeny phage are present in the sample, progeny phage may bind to the phage specific antibodies located on an external surface of the particle. Phage bound particles in a sample may be analyzed with, for example, a lateral flow device, as described in more detail below. As the sample flows through the device, the phage bound particles can further bind to anti-phage antibodies immobilized on the device, thereby creating a particle-phage-antibody conjugate. Alternatively, the progeny phage can be immobilized on a solid surface and then introduced to the particle, thereby creating a particle-phage -antibody conjugate. It can be appreciated that other methods resulting in a particle-phage-antibody conjugate are contemplated by and envisioned to be within the scope of the disclosure. The particles can then be detected by Raman spectroscopy. Presence or absence and possibly quantity of progeny phage can be detected based on the Raman spectrum that is produced by the reporter molecule coating of the particle. Further, because a single Raman spectrum can display the signal from reporter molecules that have characteristic Raman spectra, multiple particles with specific reporter molecules can be distinguished in this multiplexed format. That is, several types of phage can be amplified and their progeny detected by creating a phage-type specific particle with a reporter molecule coating or reporter molecule that is specific to each phage type. Thus, the detection method can multiplex several different types of phages.

Figure 2:
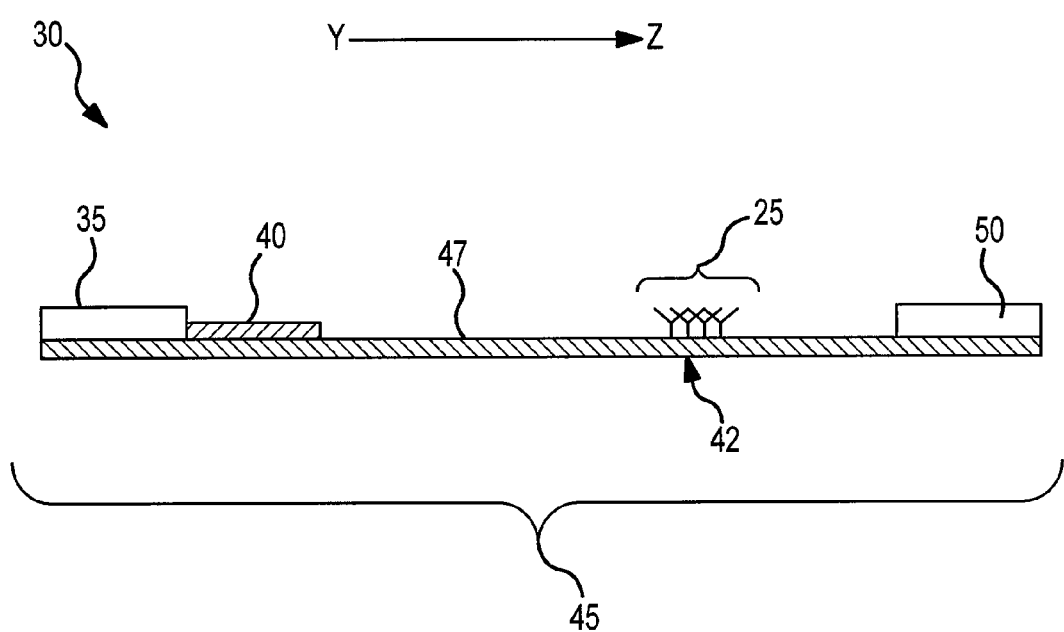
FIG. 2 depicts an embodiment of a modified lateral flow device.
Figure 3:
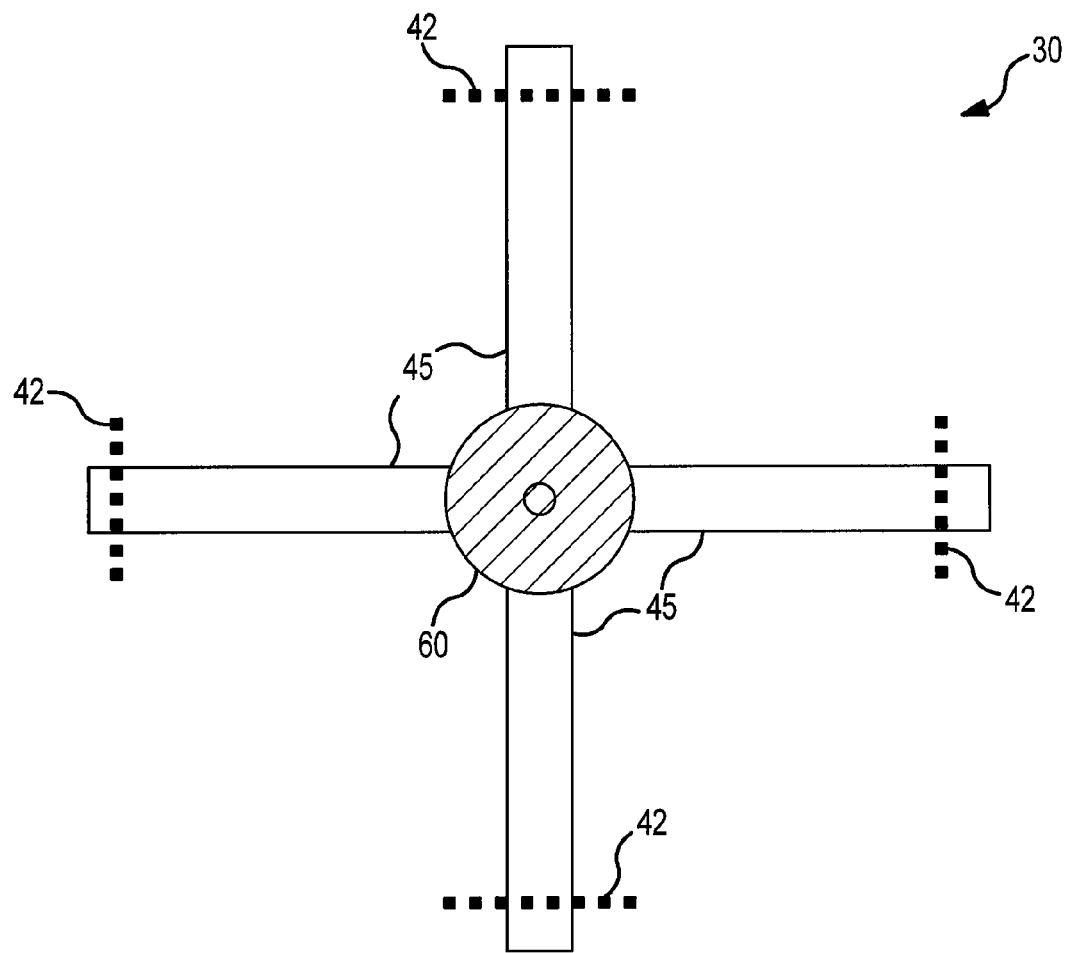
FIG. 3 depicts an alternative embodiment of a modified lateral flow device, which can be used for multiplexing.

For a discussion of alternative embodiments of the lateral flow device, reference is made to FIGS. 2 and 3. FIG. 2 depicts an embodiment of a modified lateral flow device 30. FIG. 3 depicts an alternative embodiment of a lateral flow device 30 which can be used for multiplexing.

As shown in FIG. 2, in one embodiment, the lateral flow device 30 can include a sample application pad 35, a reagent pad 40, a lateral flow strip 45, a flow zone 47, a capture surface or detector strip 42 with phage-specific antibodies 25, and an absorption pad 50.

As can be understood from FIG. 2, the sample application pad 35 and reagent pad 40 can be located at a first end of the lateral flow strip 45 of the lateral flow device 30. An absorption pad 50 is located at a second end of the lateral flow strip 45 of the lateral flow device 30. A capture surface 42 with immobilized phage-specific antibodies 25 can be between the first and second ends of the lateral flow strip 45. A flow zone 47 can also be located between the first and second ends of the lateral flow strip 45. Overall, the lateral flow device 30 operates under the principle that progeny phage present in a sample (typically an aqueous environment) will begin to diffuse generally in the direction "Y" to "Z" via the flow zone 47, e.g., a nitrocellulose membrane, away from the sample application pad 35 toward the absorbent pad 50. In one embodiment, the progeny phage can be bound to a particle prior to an introduction to the sample application pad. In an alternative embodiment, the particle is not introduced to the progeny phage prior to introduction on a sample application pad.

An aliquot of a sample, which can include progeny phage, can be placed on the sample application pad 35 and flow begins to proceed across the reagent pad 40 and toward the absorption pad 50. Samples are usually aqueous, although powdered or solid sample can be administered after dissolution or partial dissolution in an appropriate solvent, e.g., tris-based buffer or the like. The sample passes across the capture surface 42. If progeny phage are present in the sample, the phage can bind with the immobilized antibodies, thus creating a phage-antibody conjugate. A sample including the particle can then be introduced to the sample application pad 35 and as the sample passes across the capture surface, the particle can bind to the phage-antibody conjugate.

As discussed previously, the phage may already be bound to the particle prior to introduction to the sample application pad. In such a case, the particle-phage conjugate in the sample passes across the capture surface and a binding event can occur, thus creating a particle-phage-antibody conjugate. It can be appreciated that other methods resulting in a particle-phage-antibody conjugate are contemplated by and envisioned to be within the scope of the disclosure. Diffusion of the sample from the sample application pad 35 to the capture surface 42 typically takes from two to ten minutes, more preferably from two to six minutes and most preferably from about two to five minutes. The particle of the particle-phage-antibody conjugate is then detected by a Raman spectrometer. As discussed previously, in alternative embodiments, the particle can be detected by any other monochromator or spectrometer or any other optical detection methods known in the art.

The Raman spectrum produced is specific to the type of reporter molecule 15. Thus, the success of amplification and quantity of progeny phage can be detected based on the presence and/or strength of the Raman spectrum. Note also that one or more wash steps can be incorporated into the assay to facilitate removal of non-bound progeny phage and thereby lower the level of non-specific binding or background within each sample run.

As described previously, the progeny phage can be detected by contacting the phage with an antibody specific to the phage. The antibody can be immobilized on a solid surface, thus immobilizing the phage on the solid surface. The phage can also be contacted with the phage specific antibody presenting particle as described previously and the particle can be detected by Raman spectroscopy to detect, that is, determine the presence or absence of, the phage. The solid surface can be a lateral flow strip and the lateral flow strip can have at least one capture surface or detector strip. In an alternative embodiment, there can be more than one lateral flow strip, each with a single detector strip. In another alternative embodiment, there can be more than one lateral flow strips, each with more than one detector strip. In still another alternative embodiment, there can be a single lateral flow strip and the lateral flow strip can have more than one capture surface or detector strip.

In another embodiment, the lateral flow device for detection of phage amplification can include a phage specific antibody presenting particle, at least one amplified phage conjugated to the particle, and a solid support. The solid support can include a stationary phase and a phage specific antibody immobilized on the stationary phase. The antibody binds to the at least one phage. In an alternative embodiment, the solid support is at least one lateral flow strip. The lateral flow strip can have one or more detector strips. In an alternative embodiment, the solid support is a dipstick. The dipstick can have one or more detector strips. In another alternative embodiment, the stationary phase is a solid column. In another alternative embodiment, the stationary phase is at least one well in a multi-well plate.

For a description of a lateral flow device that can be used to multiplex several phages, reference is now made to FIG. 3. As shown in FIG. 3, the lateral flow device 30 includes several of lateral flow strips 45 operatively connected at an attachment end 60 to a central point. The lateral flow strips 45 can be arranged radially around a central point, that is, each strip 45 is operatively connected to a central point at one end of the strip 45. In one embodiment, the central point can be a Raman spectrometer. In an alternative embodiment, the central point can also be a central location which provides an access point for a single spectrometer, such as a Raman spectrometer. Each lateral flow strip 45 can have one or more detector strips or capture surfaces 42.

As can be understood from FIG. 3 and with reference to FIG. 1, the particle 5 can include a reporter molecule 15 wherein different reporter molecules 15 will produce a different Raman signal. By way of example only, a particle 5 with reporter molecule coating A is conjugated to phage specific antibody A and antibody A is also immobilized on the capture surface 42. A solution that can include progeny of phage A is introduced to the lateral flow device 30 at the sample application pad 35. Flow proceeds across the test strip 45 toward the absorption pad 50. If progeny of phage A are present, they can conjugate to the "A" antibodies immobilized on the capture surface 42, creating an antibody-phage conjugate.

A second solution, containing a particle 5 can then be introduced to the lateral flow device 30 at the sample application pad 35. Flow proceeds across the test strip 45 toward the absorption pad 50. The antibody-phage conjugate can further conjugate to this particle 5, thus creating an antibody-phage-particle conjugate. In an alternative embodiment, the particle 5 and the progeny phage can be introduced in the same solution, thereby creating a particle-phage conjugate, and then the particle-phage conjugate can be introduced to the sample application pad 35. Flow proceeds in the direction of the immobilized antibody 42. The particle-phage conjugate can then conjugate with the antibody 25, thereby creating a particle-phage-antibody conjugate. The particle 5 can now be detected by a Raman spectrometer to detect phage amplification.

Additionally, a particle 5 with reporter molecule coating B is conjugated to phage specific antibody B and antibody B is immobilized on the capture surface 42. A solution that can include progeny of phage B is introduced to the lateral flow device 30 at the sample application pad 35. Flow proceeds across the test strip 45 toward the absorption pad 50. If progeny of phage B are present, they can conjugate to the antibodies 25 immobilized on the capture surface 42 creating an antibody-phage conjugate. A second solution, containing a particle 5 with a second type of reporter molecule coating can then be introduced to the lateral flow device 30 at the sample application pad 35. Flow proceeds across the test strip 45 toward the absorption pad 50. The antibody-phage conjugate can conjugate to this particle 5 creating an antibody-phage-particle conjugate.

As above, in an alternative embodiment, the particle 5 and the progeny phage can be introduced in the same solution, thereby creating a particle-phage conjugate, and then the particle-phage conjugate can be introduced to the sample application pad 35. Flow proceeds in the direction of the immobilized antibody 42. The particle-phage conjugate can then conjugate with the antibody 25, thereby creating a particle-phage-antibody conjugate. The particles 5 can now be detected by a Raman spectrometer to detect phage amplification.

In an exemplary multiplex approach, samples "A" and "B" can be separately detected at different locations of the flow strip. Samples "A" and "B" can be in the same solution or can be in separate solutions. Further, the phage can be introduced to the appropriate particles at this step to create a particle-phage conjugate or after the phage has been introduced to the immobilized antibody. Thus, the "A" sample and the "B" sample can be introduced to the same lateral flow strip 45 or a different or separate lateral flow strip 45 of a lateral flow device 30. That is, the A antibodies and the B antibodies and a particle-phage-antibody A conjugate and a particle-phage-antibody B conjugate can be immobilized on the same strip 45 or on a different strip 45. The spectrum produced by reporter molecule coating A can indicate the presence and amplification of progeny of phage A. The particles on the single or multiple lateral flow strips 45 can be detected by Raman spectroscopy and the spectra produced can be analyzed.

Although the invention has been described with reference to certain embodiments, persons skilled in the art will recognize that changes can be made in form and detail without departing from the spirit and scope of the subject matter disclosed herein.

All references disclosed herein are incorporated by reference as if the disclosure of each was expressly disclosed.

What is claimed is:

1. A lateral flow device for detection of phage amplification comprising:
   at least one phage specific antibody presenting particle attached to at least one lateral flow strip; and
   a Raman spectrometer operably associated with the at least one lateral flow strip to identify said particle to detect phage amplification, wherein the at least one lateral flow strip is configured to be detected by a single Raman source and wherein the phage specific antibody presenting particle comprises:
   a coating comprising at least one reporter molecule attached to the surface of a metal nanoparticle core;
   a glass coating attached to the surface of said coating; and
   a phage specific antibody attached to the surface of said glass coating.

2. The lateral flow device of claim 1, wherein the at least one lateral flow strip is arranged radially around said Raman spectrometer.

3. The lateral flow device of claim 2, wherein the at least one lateral flow strip is operably associated with the Raman spectrometer at an attachment end.

4. The lateral flow device according to claim 1, wherein the at least one phage specific antibody presenting particle includes a coating comprising a metal oxide.

5. A lateral flow device for multiplexing analysis comprising:
   at least one lateral flow strip;
   at least one phage specific antibody presenting particle with a first type of reporter molecule coating and at least one phage specific antibody presenting particle with a second type of reporter molecule coating operably associated with said at least one lateral flow strip; and
   a Raman spectrometer operably associated with said at least one lateral flow strip to identify said particle to detect phage amplification, wherein the strip is arranged so it can be detected by a single Raman source, and wherein the phage specific antibody presenting particle comprises:
   a coating comprising at least one reporter molecule attached to the surface of a metal nanoparticle core;
   a glass coating attached to the surface of said coating; and
   a phage specific antibody attached to the surface of said glass coating.

6. The lateral flow device of claim 5, wherein the at least one lateral flow strip has multiple detector strips.

7. The lateral flow device of claim 5, wherein the at least one lateral flow strip is arranged radially around said Raman spectrometer.

8. The lateral flow device of claim 5, wherein the at least one flow strip is operably associated with the Raman spectrometer.

9. The lateral flow device according to claim 5, wherein the at least one phage specific antibody presenting particle includes a coating comprising a metal oxide.

10. A lateral flow device for detection of phage amplification comprising:

a particle comprising a phage specific antibody presenting particle and a first phage specific antibody attached to the particle;

at least one amplified phage conjugated to said particle; and a solid support comprising:

a stationary phase; and a second phage specific antibody immobilized on said stationary phase, wherein said second antibody binds to said at least one of said phage, and wherein the phage specific antibody presenting particle comprises:

a coating comprising at least one reporter molecule attached to the surface of a metal nanoparticle core;

a glass coating attached to the surface of said coating; and a phaqe specific antibody attached to the surface of said glass coating.

11. The lateral flow device according to claim 10, wherein the solid support is a solid column.

12. The lateral flow device according to claim 10, wherein the solid support is at least one well in a multi-well plate.

13. The lateral flow device according to claim 10, wherein the phage specific antibody presenting particle includes a coating comprising a metal oxide.

14. A method of detecting phage amplification comprising:

adding a progeny phage to at least one lateral flow strip, wherein the lateral flow strip includes at least one phage specific antibody immobilized to said lateral flow strip;

contacting the progeny phage with at least one phage specific antibody presenting particle to create a phage-particle complex, wherein the phage specific antibody presenting particle comprises:

a coating comprising at least one reporter molecule attached to the surface of a metal nanoparticle core;

a glass coating attached to the surface of said coating; and a phage specific antibody attached to the surface of said glass coating;

interrogating the lateral flow strip with a Raman spectrometer; and identifying said phage-particle complex to detect phage amplification.

* * * * *